(12) United States Patent
Binder (10) Patent No.: US 7,491,854 B2
(45) Date of Patent: Feb. 17, 2009

(54) ENZYMATIC METHOD OF MAKING ALDEHYDES FROM FATTY ACIDS

(75) Inventor: Thomas P. Binder, Decatur, IL (US)

(73) Assignee: Archer-Daniels-Midland Company, Decatur, IL (US)

(*) Notice: Subject to any disclaimer, the term of this patent is extended or adjusted under 35 U.S.C. 154(b) by 0 days.

(21) Appl. No.: 11/748,987

(22) Filed: May 15, 2007

(65) Prior Publication Data

US 2007/0281345 A1 Dec. 6, 2007

Related U.S. Application Data

(60) Provisional application No. 60/809,349, filed on May 31, 2006.

(51) Int. Cl.
C07C 45/41 (2006.01)
C12N 9/00 (2006.01)

(52) U.S. Cl. .................. 568/484; 435/183; 435/189

(58) Field of Classification Search .............. 568/484; 435/183, 189
See application file for complete search history.

(56) References Cited

U.S. PATENT DOCUMENTS

| | | | |
|---|---|---|---|
| 3,137,540 A * | 6/1964 | Osugi et al. | 8/115.56 |
| 5,219,733 A | 6/1993 | Myojo et al. | |
| 5,795,759 A | 8/1998 | Rosazza et al. | |
| 6,261,814 B1 * | 7/2001 | Rosazza et al. | 435/147 |
| 2004/0180400 A1 | 9/2004 | Rosazza et al. | |

FOREIGN PATENT DOCUMENTS

| | | |
|---|---|---|
| EP | 0 187 525 A2 | 7/1986 |
| JP | 64-086884 | 3/1989 |
| JP | 2005-104989 | 4/2005 |
| WO | WO 98/40472 A2 | 9/1998 |
| WO | WO 2006/012917 A1 | 2/2006 |

OTHER PUBLICATIONS

Li et al. The carboxylic acid reduction pathway in Nocardia. Purification and characterization of the aldehyde reductase.☐☐Journal of Industrial Microbiology & Biotechnology, 2000, vol. 25, pp. 328-332.*
Ando, T., et al., "Mass Spectra of Lepidoterous Sex Pheromones with a Conjugated Diene System," *Agric. Biol. Chem.* 52:1415-1423, Argricultural Chemical Society of Japan (1998).
Arfmann, H., and Abraham, W., "Microbial Reduction of Aromatic Carboxylic Acids, " *Z. Naturforsch* 48:52-57, Verlag der Zeitschrift für Naturforschung (1993).
Bachman, D.M., et al., "Reduction of Salicylate to Saligenin by Neurospora," *Arch. Biochem. Biophys.* 91:326, Academic Press (1960).
Bartelt, R.J., et al., "(Z)-5-Tetradecen-1-OL: A Secondary Phermomone of the Yellowheaded Spruce Sawfly, and Its Relationship to (Z)-10-Nonadecenal," *J. Chem. Ecol.* 9:1343-1352, Kluwer Academic/Plenum Publishers (1983).

Batista-Pereira, L., et al., "Eletrophysiological Studies and Identification of Possible Sex Pheromone Components of Brazilian Populations of the Sugarcane Borer, *Diatraea saccharalis*," *Z. Naturforsch.* 57:753-758, Verlag der Zeitschrift für Naturforschung (2002).
Bierl-Leonhardt, B.A., et al., "Location of Double-Bond Position in Long-Chain Aldehydes and Acetates by Mass Spectral Analysis of Epoxide Derivatives," *J. Chromatogr. Sci.* 18:364-367, Preston Technical Abstracts (1980).
Blum, M.S., et al., "Biochemistry of termite defense: *Coptotermes, Rhinotermes* and *Cornitermes* Species, " *Comp. Biochem. Physiol.* 71B:731-733, Pergamon Press (1982).
Brand, M., et al., "The Chemistry of the Defensive Secretion of the Beetle, *Drusilla Canaliculata*, " *J. Insect Physiol.* 19:369-382, Pergamon Press (1973).
Brühl, L., eds., "AOCS Recommended Practice Cd 1c-85 : Calculated Iodine Value," in *Official Methods and Recommended Practices of the American Oil Chemists' Society*, Fifth Edition, AOCS Press, Champaign, IL (1997).
Cavill, G.W., et al., "An Argentine ant aggregation factor," *Experientia* 35:989-990, Birkhäuser Verlag (1979).
Chen, Y. and Rosazza, J., "Microbial Transformation of Ibuprofen by a *Nocardia* Species," *Appl. Environ. Microbiol.* 60:1292-196, American Society for Microbiology (1994).
Cossè, A., et al., "Pheromone Components of the Wheat Stem Sawfly: Identification, Electrophysiology, and Field Bioassay," *J. Chem. Ecol.* 28:407-423, Kluwer Academic/Plenum Publishers (2002).
Crouch, D. and Ramsey, H., "Oxidation of Glucose by *Hydrogenomonas facilis*," *J. Bacteriol.* 84:1340-1341, American Society for Microbiology (1962).
Day, J., and Goldfine, H., "Partial Purification and Properties of Acyl-CoA Reductase from *Clostridium butyricum*," *Arch. Biochem. Biophys.* 190:322-331, Academic Press (1978).
Easton, E., et al., "Polyunsaturated Nitroalkanes and Nitro-Substituted Fatty Acids," *Synthesis* 3:451-457, Thieme Stuttgart (2001).
Einhorn, J. and Tabet, J., "From CI-NO$^+$/MS to CI-NO$^+$/MS-MS to Locate an Epoxide in Long Chain Epoxide-Acetates, Alcohols and Aldehydes," *Spectros. Int. J.* 5:281-288, the J.R.J. Paré Establishment for Chemistry Ltd. (1987).
El-Sayed, A. M., "The Pherobase: Database of Insect Pheromones as Semiochemicals", retrieved from HTTP://WWW.PHEROBASE.COM on Feb. 27, 2008.
Frerot, B. and Demolin, G., "Sex pheromone of the processionary moths and biosystematic considerations within the genus *Thaumetopoea (Thaumetopoeidae Thaumetopoeinae)*," *Boll. Zool. Agr. Bachic.* 25:33-40, Unione Zoologica Italiana (1993).
Gross, G., "Formation and Reduction of Intermediate Acyladenylate by Aryl-Aldeyhyde NADP Oxidoreductase from *Neurospora crassa*," *Eur. J. Biochem.* 31:585-592, Blackwell Science Ltd. (1972).

(Continued)

*Primary Examiner*—Sikarl A Witherspoon
(74) *Attorney, Agent, or Firm*—Sterne, Kessler, Goldstein & Fox P.L.L.C.

(57) ABSTRACT

The present invention provides methods of enzymatically preparing aldehydes from fatty acids by utilizing a carboxylic acid reductase enzyme to reduce the fatty acids to their corresponding aldehydes. The present invention also provides aldehydes prepared by the methods of the invention.

19 Claims, 5 Drawing Sheets

OTHER PUBLICATIONS

Gross, G., and Zenk, M., "Reduktion aromatischer Säuren zu Aldehyden und Alkoholen im zellfreien System. 1. Reinigung und Eigenschaften von Aryl-Aldehyd: NADP-Oxidoreduktase aus *Neurospora crassa*," *Eur. J. Biochem* 8:413-419, Blackwell Science Ltd. (1969).

Gross, G., and Zenk, M., "Reduktion aromatischer Säuren zu Aldehyden und Alkoholen im zellfreien System. 2. Reinigung und Eigenschaften von Arly-Alkohol: NADP-Oxidoreduktase aus *Neurospora crassa*," *Eur. J. Biochem.* 8:420-425, Blackwell Science Ltd. (1969).

Hansen, C.M., "Solubility Parameters- An Introduction" in *Hansen Solubility Parameters*, CRC Press, Boca Raton, FL, pp. 5-6, 22, and 82 (2000).

Hempel, J., et al., "Aldeyhyde dehydrogenases: Widespread structural and functional diversity within a shared framework," *Protein Sci.* 2:1890-1900, Cold Spring Laboratory Press (1993).

Holmeide, A., et al., "The syntheses of three highly unsaturated marine lipid hydrocarbons," *J. Chem. Soc., Perkin Trans. 1*:1942-1946, The Royal Society of Chemistry (2001).

Hui, H., eds., "Industrial and Consumer Nonedible Products from Oils and Fats," in *Bailey's Industrial Oil and Fat Products*, John Wiley & Sonds, Inc., New York, NY, pp. 33, 36-37, 52-63 and 91 (1996).

Jackson, B., "Dufour Gland Contents of Three Species of *Myrmecia* (Hymenoptera: Formicidae), Primitive Ants of Australia," *J. Chem. Ecol. 15*:2191-2205, Kluwer Academic/Plenum Publishers (1989).

Ježo, I. and Zemek, J., "Enzymatische Reduktion einiger aromatischer Carboxysäuren," *Chem. Papers 40*:279:-281, American Chemical Society (1986).

English Language Abstract for Ježo, I. and, Zemek, J., *Chem. Papers 40*:279-281 (listed herewith as document NPL27).

Kato, N., et al., "Microbial Reduction of Benzoate to Benzyl Alcohol," *Agric. Biol. Chem. 52*:1885-1886, Agricultural Chemical Society Of Japan (1988).

Kato, N., et al., "Purification and Characterization of Aromatic Acid Reductase from *Nocardia asteroides* JCM 3016," *Agric. Biol. Chem. 55*:757-762 Agricultural Chemical Society Of Japan (1991).

Kaufmann, H., and Jansen, H., "Über $C_{18}$ -Polyhydroxy-Fettsäuren und- Fettaldehyde," *Chem. Ber. 92*:2789-2797, Verlag Chemie (1959).

English Lanquage Abstract for Kaufmann, H., and Jansen, H., *Chem. Ber. 92*:2789-2797 (listed herewith as document NPL31).

Kaufmann, H. and Kirschnek, H., "Zur Kenntnis der Fettaldehyde IV: Darstellung mehrfach ungesättigter Fettaldehyde," *Fette, Seifen, Anstrichmittel 12*:1125-1131 (1958).

Li, T. and Rosazza, J., "NMR Identification of an Acyl-adenylate Intermediate in the Aryl-aldehyde Oxidoreductase Catalyzed Reaction," *J. Biol. Chem. 273*:34230-34233, American Society for Chemistry and Molecular Biology (1998).

Li, T. and Rosazza, P., "The carboxylic acid reduction pathway in *Nocardia*. Purification and characterization of the aldehyde reductase," *J. Ind. Microbiol. Biotechnol. 25*:328-332, Nature Publishing Group (2000).

Levinson, H. and Mori, L., "The Pheromone Activity of Chiral Isomers of Trogodermal for Male Khapra Beetles," *Naturwissenschaften 67*:148-149, Springer-Verlag (1980).

Leal, W., et al., "Identification, Synthesis, and Field Evaluation of the Sex Pheromone from the Citrus Leafminer, *Phyllocnistis citrella*," *J. Chem. Ecol. 32*:155-168, Kluwer Academic/Plenum Publishers (Jan. 2006).

Lloyd, H., et al., "Chemistry of Mandibular and Dufour's Gland Secretions of Ants in Genus *Myrmecocystus*," *J. Chem. Ecol. 15*:2589-2599, Kluwer Academic/Plenum Publishers (1989).

McDaniel, C., et al., "Chemistry of Male Mandibular Gland Secretions of *Philanthus basilaris* Cresson and *Philanthus bicinctus* (Mickel) (Hymenoptera:Sphecidae)," *J. Chem. Ecol. 13*:227-235, Kluwer Academic/Plenum Publishers (1987).

McDaniel, C., et al.,"Mandebular Gland Secretions of the Male Beewolves *Philanthus crabroniforms, P. barbatus*, and *P. pulcher* (Hymenoptera: Sphecidae)," *J. Chem. Ecol. 18*:27-37, Kluwer Academic/Plenum Publishers (1992).

Millar, J., et al., "Unusual Acetylenic Sex Pheromone of grape Leaffoolder (Lepidoptera: Pyralidae)," *J. Econ. Entomol. 95*:692-698, Entomological Society of America (2002).

Morris, B., et al., "Identification of 1-Octacosanal and 6-Methoxy-2-Benzoxazolinone from Wheat as Ovipositional Stimulants for Hessian Fly," *J. Chem. Ecol. 26*:859-873, Kluwer Academic/Plenum Publishers (2000).

Nagayama, K., et al., "Direct Hydrogenation of Carboxylic Acids to Corresponding Aldehydes Catalyzed by Palladium Complexes," *Bull. Chem. Soc. Jpn. 74*:1803-1815, Nippon Kagakukai (2001).

Nelson, D. and Fatland, C., "Very Long-Chain Methyl-Branched Alcohols and Their Acetate Esters in the Internal Lipids of Lepidopteran Pupae: *Cochylis hospes, Diatraea grandiosella, Homoeosoma electellum, Heliothis virescens* and *Helicoverpa zea*," *Comp. Biochem. Physiol. 11*:243-256, Elsevier Science (1997).

Nishida, T., et al., "Synthesis and Characterization of Hexadecadienyl Compounds with a Conjugated Diene System, Sex Pheromone of the Persimmon Fruit Moth and Related Compounds," *Biosci. Biotechnol. Biochem. 67*:822-829, Japan Society for Bioscience, Biotechnology, and Agrochemistry (2003).

Okuno, S., et al., "Syntheses and Biological Activities of Photolabile Indolactam Derivatives; New Probes for the Receptor Analysis of Tumor Promotes," *Agric. Biol. Chem 54*:1885-1887, Agricultural Chemical Society Of Japan (1990).

Patricio, E., et al., "Secretions of stingless bees: the Dufour glands of some *Frieseomelitta* species (Apidae, Meliponinae)," *Apidologie 34*:359-365, Arbetisgemeinschaft der Institute für Bienenforschung [et] Institut national de la recherche agronomique (2003).

Prestwich, G. and Collins, M., "3-Oxo-(Z)-9-hexadecenal: An Unusual Enolic β-Keto Aldehyde from a Termite Soldier Defense Secretion," *J. Org. Chem. 46*:2283-2385, American Chemical Society (1981).

Prestwich, G. and Collins, M., "Chemical Defense Secretions of the Termite Soldiers of *Acorhinotermes* and *Rhinotermes* (Isoptera, Rhinotermitinae): Ketones, Vinyl Ketones, and β- Ketoaldehydes Derived from Fatty Acids," *J. Chem. Ecol. 8*:147-161, Kluwer Academic/Plenum Publishers (1982).

Quintana, A., et al "Interspecific Variation in Terpenoid Composition of Defensive Secretions of European *Reticulitermes* Termites," *J. Chem. Ecol. 29*:639-652, Kluwer Academic/Plenum Publishers (2003).

Raman, T. and Shanmugasundaram, E., et al., "Metabolism of Some Aromatic Acids by *Aspergillus Niger*," *J. Bacteriol. 84*:1339-1340, American Society for Microbiology (1962).

Reed, D. and Chisholm, M., "Attraction of Moth Species of Tortricidae, Gelechiidae, Geometridae, Drepanidae, Pyralidae, and Gracillariidae Families to Field Traps Baited with Conjugated Dienes," *J. Chem. Ecol. 11*:1645-1657, Kluwer Academic/Plenum Publishers (1985).

Riendeau, D. and Meighen, E., "Enzymatic reduction of fatty aids and acyl-CoAs to long chain aldehydes and alcohols," *Experientia 41*:707-713, Birkhäuser Verlag (1985).

Riendeau, D. and Meighen, E., "Fatty acid reductase in bioluminescent bacteria. Resolution from aldehyde reductases and characterization of the aldehyde product," *Can. J. Biochem. 59*:440-446, National Research Council Of Canada (1981).

Ritter, F., et al., "Trail Pheromone of the Pharaoh's Ant, *Monomorium Pharaonis*: Isolation and Identification of Faranal, a Terpenoid Related to Juvenile Hormone II," *Tetrahedron Lett. 30*:2617-2618, Elsevier (1977).

Rossi, R., et al., "Chirality influences the biological activity of the sex pheromones of the khapra beetle," *Naturwissenschaften. 66*:211, Springer-Verlag (1979).

Santangelo, E., et al., "Identification,Syntheses, and Characterization of the Geometric Isomers of 9,11-Hexadecadienal from Female Pheromone Glands of the Sugar Cane Borer *Diataea saccharalis*," *J. Nat. Prod. 65*:909-915, American Society of Pharmacognosy (2002).

Schmidt, J., et al., "Volatiles from Mandibular Glands of Male Beewolves (Hymenoptera:Sphecidae, *Philanthus*) and Their Possible Roles," *J. Chem. Ecol. 11*:895-901, Kluwer Academic/Plenum Publishers (1985).

Silverstein, R., et al., "Perception by *Trogoderma* Species of Chirality and Methyl Branching at a Site Far Removed From a Functional Group in a Pheromone Component," *J. Chem. Ecol.* 6:911-917, Kluwer Academic/Plenum Publishers (1980).

Stevenson, D., et al., "Pecan Nut Casebearer Pheromone Monitoring and Degree-Day Model Validation Across the Pecan Belt," *Southwestern Entomologist Suppl 27*:57-73, The Society of Southwestern Entomologists (2003).

Swedenborg, P. and Jones, R., "(Z)-4-Tridecenal, A Pheromonally Active Air Oxidation Product from a Series of (Z,Z)-9,13 Dienes in *Macrocentrus grandii* Goidanich (Hymenoptera: Braconidae)," *J. Chem. Ecol. 18*:1913-1931, Kluwer Academic/Plenum Publishers (1992).

Szöcs, G., et al., "2,13- and 3,13-Octadecadienyl Compounds Composing Sex Attractants for Tineid and Sesiid Moths (Lepidoptera)," *Biochem. Syst. Ecol. 17*:417-422, Pergamon Press (1989).

Tsuda, Y., et al., "Asymmetric Reduction of 2-Methyl-2-aryloxyacetic Acids by Glomerella cingulata," *Agric. Biol. Chem. 48*:1373-1374, Agricultural Chemical Society Of Japan (1984).

Tsuda, Y., et al., "Microbial Reduction of 2-Phenylpropionic Acid, 2-Benzyloxypropionic Acid and 2-(2-Furfuryl)propionic Acid," *Chem. Pharm. Bull. 11*:4657-4661, Pharmaceutical Society of Japan (1985).

Venkitasubramanian, P., "Biocatalytic Reduction of Carboxylic Acids: Mechanism and Applications," in *Biocatalysis in the Pharmaceutical and Biotechnology Industries*, CRC Press, Boca Raton, Florida, pp. 425-440 (Sep. 2006).

White, H., et al., "Carboxylic acid reductase; a new tungsten enzyme catalyses the reduction of non-activated carboxylic acids to aldehydes," *Eur. J. Biochem. 184*:89-96, Blackwell Science Ltd. (1989).

White, H., et al., "On a reversible molybdenum-containing aldehyde oxidoreductase from *Clostridium formicoaceticum*," *Arch. Microbiol. 159*:244-249, Springer-Verlag (1993).

Witzgall, P., et al., "The Pherolist", retrieved from WWW-PHEROLIST.SLU.SE/ on Feb. 27, 2008.

International Search Report for International Application No. PCT/US2007/011556, mailed on Dec. 11, 2007, European Patent Office, Netherlands.

English Language Abstract for JP 64-086884, Patent Abstracts of Japan (listed on accompanying document PTO/SB/08A as document FP2).

English Language Abstract for JP 2005-104989, Patent Abstracts of Japan (listed on accompanying document PTO/SB/08A as document FP4).

Bouquet, F. and Paquot, C., "Etude des acyloïnes grasses suppérieures et de quelques dérivés," *Bull. Soc. Chim. Fr. 5*:440-441, Masson Et Cie (1949).

* cited by examiner

ENZYMATIC METHOD OF MAKING ALDEHYDES FROM FATTY ACIDS

CROSS-REFERENCE TO RELATED APPLICATIONS

This applications claims the benefit, under 35 U.S.C. § 119(e), of the earlier filing date of U.S. Provisional Application No. 60/809,349, filed on May 31, 2006, the entire contents of which are incorporated herein by reference.

BACKGROUND OF THE INVENTION

1. Field of the Invention

The present invention is directed to enzymatic methods of preparing aldehydes from fatty acids.

2. Description of Related Art

Microorganism-produced enzymes are widely used as a class of biocatalytic reagents in synthetic organic chemistry in a variety of reactions including, e.g., oxidations, reductions, hydrolyses, and carbon-carbon bond ligations. For example, enzyme reactions catalyzed by esterases may be used either hydrolytically or to synthesize esters, depending on whether the reaction medium is aqueous or organic in composition.

Biocatalysts are valued for their intrinsic abilities to bind organic substrates and to catalyze highly specific and selective reactions under the mildest of reaction conditions. These selectivities and specificities are realized because of highly rigid interactions occurring between the enzyme active site and the substrate molecule. Biocatalytic reactions are particularly useful when they are used to overcome difficulties encountered in catalysis achieved by the use of traditional chemical approaches.

The reduction of carboxylic acids by microorganisms is a relatively new biocatalytic reaction that has not yet been widely examined or exploited. Jezo and Zemek reported the reduction of aromatic acids to their corresponding benzaldehyde derivatives by *Actinomycetes in Chem. Papers* 40(2): 279-281 (1986). Kato et al. reported the reduction of benzoate to benzyl alcohol by *Nocardia asteroides* JCM 3016 (*Agric. Biol. Chem.* 52(7):1885-1886 (1988)), and Tsuda et al. described the reduction of 2-aryloxyacetic acids (*Agric. Biol. Chem.* 48(5):1373-1374 (1984)) and arylpropionates (*Chem. Pharm. Bull.* 33(11):4657-4661 (1985)) by species of *Glomerella* and *Gloeosporium*. Microbial reductions of aromatic carboxylic acids, typically to their corresponding alcohols, have also been observed with whole cell biotransformations by *Clostridium thermoaceticum* (White et al., *Eur. J. Biochem.* 184:89-96 (1989)) and by *Neurospora* (Bachman et al., *Arch. Biochem. Biophys.* 91:326 (1960)). More recently, carboxylic acid reduction reactions have reportedly been catalyzed by whole cell preparations of *Aspergillus niger, Corynespora melonis* and *Coriolus* (Arfmann et al., *Z. Naturforsch* 48c:52-57 (1993); cf., Raman et al., *J. Bacteriol* 84:1340-1341 (1962)), and by *Nocardia* (Chen and Rosazza, *Appl. Environ. Microbiol.* 60(4):1292-1296 (1994)).

Carboxylic acid reductases are complex, multicomponent enzyme systems requiring the initial activation of carboxylic acids via formation of acyl-AMP and often coenzyme A intermediates (see, e.g., Hempel et al., *Protein Sci.* 2:1890-1900 (1993). The enzymatic reaction offers significant advantages over existing methods used in chemical reductions of carboxylic acids or their derivatives. The carboxylic acid reduction reaction appears to bear the usual desirable features of functional group specificity, and it also functions well under mild reaction conditions and produces a high yield of product. The reduction of the activated carboxylic acid intermediate occurs step-wise to give aldehyde, and then alcohol, products (Gross et al., *Eur. J Biochem.* 8:413-419; 420-425 (1969); Gross, *Eur. J. Biochem.* 31:585-592 (1972)).

Fatty alcohols and aldehydes can be commercially produced using one of several methods. However, one of the most widely used commercial methods, catalytic hydrogenation of fatty acids and methyl esters from fats and oils, produces fatty alcohols using high pressures (typically, 25,000-30,000 kP) and high temperatures (typically 250-300° C.). See, e.g., "Fatty Acids and Derivatives from Coconut Oil," in *Bailey's Industrial Oil and Fat Products,* 5th ed., Volume 5, Y. H. Hui, ed., John Wiley & Sons, Inc. (1996). The high pressures and temperatures employed in these methods are harsh in comparison to the milder conditions common with enzymatic reactions and can lead to unwanted side reactions, such as isomerization of one or more double bonds present in unsaturated fatty acid starting materials.

There continues to exist a need for improved methods of producing fatty alcohols and aldehydes with improved reaction specificity that lead to higher yields and fewer side reactions.

SUMMARY OF THE INVENTION

The present invention provides enzymatic methods of preparing aldehydes from fatty acids by utilizing a carboxylic acid reductase enzyme to reduce the fatty acids to their corresponding aldehydes The present invention also provides aldehydes prepared by the methods of the invention. The carboxylic acid reductase reduces the carboxyl moiety of the fatty acid to an aldehyde moiety which a separate aldehyde reductase can then further reduce to an alcohol moiety (Tao & Rosazza, *J. Indust. Microbiol. Biotechnol.* 25: 328-332 (2000)).

Thus, the present invention is directed to a method of preparing a ($C_6$-$C_{32}$) aldehyde from a fatty ($C_6$-$C_{32}$)alkyl carboxylic acid material derived from a vegetable oil or animal oil, the method comprising contacting the fatty ($C_6$-$C_{32}$) alkyl carboxylic acid material with a carboxylic acid reductase, wherein the ($C_6$-$C_{32}$)aldehyde is prepared.

The present invention is also directed to the method of preparing a ($C_6$-$C_{32}$) aldehyde from a fatty ($C_6$-$C_{32}$)alkyl carboxylic acid material as described herein, wherein the vegetable oil is selected from the group consisting of soybean oil, linseed oil, sunflower oil, castor oil, corn oil, canola oil, rapeseed oil, palm kernel oil, cottonseed oil, peanut oil, coconut oil, palm oil, tung oil, safflower oil and derivatives, conjugated derivatives, genetically-modified derivatives and mixtures thereof.

The present invention is further directed to the method of preparing a ($C_6$-$C_{32}$) aldehyde from a fatty ($C_6$-$C_{32}$)alkyl carboxylic acid material as described herein, wherein the fatty ($C_6$-$C_{32}$)alkyl carboxylic acid material comprises a fatty ($C_6$-$C_{32}$)alkyl carboxylic acid, and wherein the fatty ($C_6$-$C_{32}$) alkyl carboxylic acid is unsaturated. The invention is also directed to the method described herein, wherein the fatty ($C_6$-$C_{32}$)alkyl carboxylic acid material comprises one or more ($C_{16}$-$C_{18}$)alkyl fatty acids.

The present invention is also directed to the method of preparing a ($C_6$-$C_{32}$) aldehyde from a fatty ($C_6$-$C_{32}$)alkyl carboxylic acid material as described herein, wherein the fatty ($C_6$-$C_{32}$)alkyl carboxylic acid material comprises one or more fatty ($C_6$-$C_{32}$)alkyl carboxylic acids independently selected from the group consisting of palmitoleic acid, oleic acid, linoleic acid, linolenic acid, eleostearic acid, ricinoleic acid, arachidonic acid, cetoleic acid, eicosapentaenoic acid, docosahexaenoic acid, erucic acid, and derivatives and mixtures thereof The present invention is also directed to the method of preparing a ($C_6$-$C_{32}$) aldehyde from a fatty ($C_6$-$C_{32}$)alkyl carboxylic acid material as described herein, wherein the fatty ($C_6$-$C_{32}$)alkyl carboxylic acid material has a hydrophilic/lipophilic balance of less than about 3.5.

The present invention is also directed to the method of preparing a ($C_6$-$C_{32}$) aldehyde from a fatty ($C_6$-$C_{32}$)alkyl carboxylic acid material as described herein, wherein the fatty ($C_6$-$C_{32}$)alkyl carboxylic acid material has a Hansen polarity value of less than about 4 (delta/sqr(MPa)) and a Hansen hydrogen bonding value of less than about 8 (delta/sqr(MPa)).

The present invention is also directed to the method of preparing a ($C_6$-$C_{32}$) aldehyde from a fatty ($C_6$-$C_{32}$)alkyl carboxylic acid material as described herein, wherein the fatty ($C_6$-$C_{32}$)alkyl carboxylic acid material has an iodine value greater than about 50.

The present invention is directed to the method of preparing a ($C_6$-$C_{32}$)aldehyde from a fatty ($C_6$-$C_{32}$)alkyl carboxylic acid material as described herein, wherein the reductase is isolated from a *Nocardia* species, a *Neurospora* species, or a *Clostridium* species. The invention is also directed to the method of preparing the ($C_6$-$C_{32}$)aldehyde, wherein the reductase is isolated from a *Nocardia* species, including *Nocardia* sp. NRRL 5646. The invention is also directed to the method wherein the reductase is a recombinant reductase.

The present invention is directed to the method of preparing a ($C_6$-$C_{32}$)aldehyde from a fatty ($C_6$-$C_{32}$)alkyl carboxylic acid material as described herein, wherein the method further comprises incubating the fatty ($C_6$-$C_{32}$)alkyl carboxylic acid material and the carboxylic acid reductase for a period of time sufficient to reduce at least about 50% of the carboxylic acid material to the ($C_6$-$C_{32}$)aldehyde. The invention is further directed to the method, further comprising separating the ($C_6$-$C_{32}$)aldehyde from the fatty ($C_6$-$C_{32}$) alkyl carboxylic acid material.

The present invention is directed to the method of preparing a ($C_6$-$C_{32}$)aldehyde from a fatty ($C_6$-$C_{32}$)alkyl carboxylic acid material as described herein, wherein the ($C_6$-$C_{32}$)aldehyde has Formula I:

I wherein, in each instance, A, B, C, R, n, and x are as defined below.

The present invention is also directed to a or ($C_6$-$C_{32}$) aldehyde made according to the method described herein, wherein the ($C_6$-$C_{32}$)aldehyde has Formula I, wherein A, B, C, R, n, and x are as defined below.

DESCRIPTION OF THE FIGURES

FIGS. 1A-1D present the results of thin layer chromatography (TLC) analysis of bacterial culture aliquots sampled at various times during the course of the in vivo reduction experiments described in Example 1. Key: Lane 1: organism control; Lane 2: oleic acid standard; Lane 3: 4 h sample; Lane 4: 8 h sample; Lane 5: 24 h sample; Lane 6: 24 h sample +oleic acid control; Lane 7: octadecanol control.

FIGS. 2A and 2B present $^1$H and $^{13}$C NMR spectra for Fraction 1 ($R_f$=0.74), as described in Example 1. FIG. 2A presents the $^1$H NMR spectrum for Fraction 1, while

DETAILED DESCRIPTION OF THE INVENTION

The present invention is directed to enzymatic methods of preparing aldehydes from their corresponding fatty acids by utilizing a carboxylic acid reductase.

In the methods of the present invention, a fatty acid is contacted with a carboxylic acid reductase, which enzymatically converts the fatty acid into its corresponding aldehyde. The carboxylic acid reductase reduces the carboxyl moiety of the fatty acid to an aldehyde moiety, which can be further reduced to an alcohol moiety. The fatty aldehydes produced by the methods of the invention and fatty alcohols produced therefrom can be used in a variety of applications. See, e.g., International Publ. No. WO 2006/012917 A1, which describes the use of fatty alcohols as plasticizers. Other applications include incorporation into existing surfactants to produce surfactants with better low temperature performance, resins, dyes, organic acids, perfumes, flavorings, adhesives, papermaking, chemical intermediates, solvents, agricultural chemicals, cosmetic and personal care products, waxes, lubricants, and additives for polymers and coatings with both hydrolytic stability and reactivity.

Thus, the present invention is directed to a method of preparing an aldehyde from a corresponding fatty acid or fatty acid material, the method comprising contacting the fatty acid or fatty acid material with a carboxylic acid reductase, wherein the aldehyde is prepared. The fatty acid or fatty acid material is typically derived from a vegetable oil or an animal oil. The fatty acid or fatty acid material also comprises one or more fatty acids that can be saturated or unsaturated.

Enzymatic conversion of fatty acids to alcohols and/or aldehydes provides a number of advantages over traditional synthetic methods of producing alcohols and aldehydes from fatty acids, such as high degree of specificity and selectivity and mild reaction conditions.

A particular advantage of the enzymatic methods of the present invention is that corresponding alcohols and/or aldehydes can be produced from fatty acids having one or more double bonds along the hydrocarbon backbone (unsaturated fatty acids) or from fatty acid derivatives, i.e., fatty acids bearing functional groups such as, e.g., a hydroxyl group, an amine group, or an epoxide ring attached to the hydrocarbon backbone.

For example, the enzymatic methods of the present invention can be used to convert a fatty acid having an epoxide group along the backbone to the corresponding alcohol and/or aldehyde containing the epoxide group at the same position along the backbone. Reactions such as these can be difficult to achieve using conventional commercial methods of converting fatty acids to alcohols.

As another example, the methods of the present invention can be used to convert an unsaturated fatty acid having one or more cis double bonds along its hydrocarbon chain to the corresponding unsaturated cis aldehyde. The aldehyde product retains the same stereochemistry at each double bond as the unsaturated fatty acid starting material, and can be further converted to an alcohol using an enzyme or other suitable catalyst.

Current methods of producing alcohols from their corresponding fatty acids can lead to isomerization of one or more double bonds in unsaturated fatty acids, resulting in contamination of the corresponding alcohol and/or aldehyde with unwanted geometric isomers. A commercially produced sample of oleic acid was recently analyzed using gas chromatography with mass spectroscopy to determine the presence and composition of geometric isomers of oleyl alcohol (C18:1 9 c), a C18 alcohol containing one cis double bond in its hydrocarbon backbone. In addition to containing small percentages of C12 alcohols (0.26% w/w), C14 alcohols (0.34% w/w), and C16 alcohols (3.74% w/w), the C18 oleyl alcohol (91.75% w/w) was found to contain significant levels of the corresponding trans isomer in the following proportions:

TABLE 1

| Isomer | % (w/w) |
|---|---|
| C18:1 cis isomer | 77.75 |
| C18:1 trans isomer | 14.02 |

Use of the methods of the present invention make possible the production of a specific cis or trans isomer of an aldehyde from the corresponding fatty acid that is uncontaminated with the corresponding unwanted geometric isomer. The carboxylic acid reductase reduces the carboxyl moiety of the fatty acid to an aldehyde moiety which a separate aldehyde reductase can then further reduce to an alcohol moiety.

The term "fatty acid" as used herein refers to a saturated or unsaturated aliphatic carboxylic acid having a hydrocarbon backbone from about 4 to about 32 carbon atoms long. The term "medium chain fatty acid" as used herein refers to a saturated or unsaturated aliphatic fatty acid, i.e., aliphatic carboxylic acid, having a hydrocarbon backbone from about 10 to about 22 carbon atoms long. The term "fatty ($C_6$-$C_{32}$) alkyl carboxylic acid" as used herein refers to a saturated or unsaturated aliphatic fatty acid, i.e., aliphatic carboxylic acid, having a hydrocarbon backbone from 6 to 32 carbon atoms long. The aliphatic hydrocarbon chain of the fatty acid can be linear or branched, but is typically linear. Examples of fatty acids useful in the present invention include, but are not limited to, palmitoleic acid, oleic acid, linoleic acid, linolenic acid, eleostearic acid, ricinoleic acid, arachidonic acid, cetoleic acid, eicosapentaenoic acid, docosahexaenoic acid, and erucic acid. The term "fatty acid" is also meant to encompass derivatives of fatty acids, including, e.g., conjugated derivatives and genetically modified derivatives of fatty acids. Examples of fatty acid derivatives useful in the present invention include, but are not limited to, fatty acids having functional groups capable of undergoing reduction, such as fatty acids having internal aldehydes, and epoxides and hydroxides of fatty acids. Such fatty acids having functional bonds capable of undergoing reduction, such as double bonds, may conveniently be sourced from genetically modified plants, such as genetically modified soybean, canola, sunflower, or other plants. Alternatively, fatty acids from milk or tissue from genetically modified animals, such as *Bos taurus*, may be useful.

The term "about," as used herein, applies to all numeric values, whether or not explicitly indicated. The term "about" generally refers to a range of numbers that one skilled in the art would consider equivalent to the recited value (i.e., having the same function or result) and may include numbers that are rounded to the nearest significant figure.

The term "fatty acid material" or "fatty ($C_6$-$C_{32}$)alkyl carboxylic acid material" as used herein refers to a composition comprising one or more fatty acids or derivatives thereof, or one or more ($C_6$-$C_{32}$)alkyl fatty acids or derivatives thereof, respectively, and typically includes mixtures of fatty acids or their derivatives. Examples of fatty acid materials include, but are not limited to, mixtures of fatty acids derived from animal or vegetable oils.

Fatty acids or fatty acid materials suitable for use in the methods of the present invention are derived from animal oils or vegetable oils, or mixtures or derivatives thereof, including, for example, conjugated derivatives and genetically-modified derivatives.

For example, in some aspects of the invention, the fatty acid or fatty acid material is derived from a vegetable oil or derivative thereof. The fatty acid or fatty acid material can be derived from triglycerides (including, e.g., triglycerides of medium chain fatty acids), diglycerides, or monoglycerides of vegetable origin, or derivatives or mixtures thereof. In some embodiments, the fatty acid or fatty acid material is enriched in double bonds and is derived from a vegetable oil such as, e.g., cocoa butter, cocoa butter substitutes, illipe fat, kokum butter, mowrah fat, phulwara butter, sal fat, shea fat, borneo tallow, canola oil, castor oil, coconut oil, coriander oil, corn oil, cottonseed oil, hazelnut oil, hempseed oil, jatropha oil, linseed oil, mango kernel oil, meadowfoam oil, mustard oil, neat's foot oil, olive oil, palm oil, palm kernel oil, peanut oil, rapeseed oil, rice bran oil, safflower oil, sasanqua oil, shea butter, soybean oil, sunflower seed oil, tall oil, tsubaki oil, tung oil, or another vegetable oil, or a derivative, conjugated derivative, genetically-modified derivative or mixture thereof. Thus, in some embodiments, the fatty acid or fatty acid material is derived from a vegetable oil selected from the group consisting of soybean oil, linseed oil, sunflower oil, castor oil, corn oil, canola oil, rapeseed oil, palm kernel oil, cottonseed oil, peanut oil, coconut oil, palm oil, tung oil, safflower oil and derivatives, conjugated derivatives, genetically-modified derivatives and mixtures thereof. In other embodiments, the fatty acid or fatty acid material is derived from triolein palm olein, palm stearin, palm kernel olein, palm kernel stearin, or a derivative, conjugated derivative, genetically-modified derivative or mixture thereof In other aspects of the invention, the fatty acid or fatty acid material is derived from an animal fat or oil or derivative thereof. Examples of animal fats and oils include, but are not limited to, butterfat, chicken fat, milk fat, lard, lanolin, beef tallow, mutton tallow, tallow, and egg yolk, and derivatives, conjugated derivatives, genetically-modified derivatives and mixtures thereof. In some embodiments, for example, the fatty acid or fatty acid material is derived from an animal fat or oil selected from the group consisting of butterfat, chicken fat, tallow, lard, and egg yolk, and derivatives, conjugated derivatives, genetically-modified derivatives and mixtures thereof. In other embodiments, the fatty acid or fatty acid material is derived from a marine or fish oil. Examples of marine or fish oils include, but are not limited to, mackerel oil, salmon oil, striped bass oil, rainbow trout oil, halibut oil, tuna oil, cod oil, cod liver oil, tilapia oil, menhaden oil, candlefish oil, orange roughy oil, pile herd oil, sardine oil, whale oil, herring oil, and derivatives, conjugated derivatives, genetically-modified derivatives and mixtures thereof.

In some aspects of the present invention, the fatty acid or fatty acid material comprises a fatty ($C_6$-$C_{32}$)alkyl carboxylic acid or a mixture of fatty ($C_6$-$C_{32}$)alkyl carboxylic acids. In other aspects, the fatty acid or fatty acid material comprises a fatty ($C_6$-$C_{30}$)alkyl carboxylic acid or a mixture of fatty ($C_6$-$C_{30}$)alkyl carboxylic acids, or a fatty ($C_6$-$C_{22}$)alkyl carboxylic acid or a mixture of fatty ($C_6$-$C_{22}$)alkyl carboxylic acids. In yet other aspects of the present invention, the fatty acid or fatty acid material comprises a fatty ($C_{16}$-$C_{22}$)alkyl carboxylic acid or a mixture of fatty ($C_{16}$-$C_{22}$)alkyl carboxylic acids. In some aspects, the fatty acid or fatty acid material comprises a fatty ($C_{16}$-$C_{20}$)alkyl carboxylic acid or a mixture of fatty ($C_{16}$-$C_{20}$)alkyl carboxylic acids thereof, or a fatty ($C_{16}$-$C_{18}$)alkyl carboxylic acid or a mixture of fatty ($C_{16}$-$C_{18}$)alkyl carboxylic acids.

Thus, in some aspects, the present invention is directed to a method of preparing a ($C_6$-$C_{32}$)aldehyde from a corresponding fatty ($C_6$-$C_{32}$)alkyl carboxylic acid material derived from a vegetable oil or an animal oil, the method comprising contacting the fatty ($C_6$-$C_{32}$)alkyl carboxylic acid material with a carboxylic acid reductase; wherein the ($C_6$-$C_{32}$)aldehyde is prepared.

Fatty acids suitable for use in the present invention can be either saturated fatty acids or unsaturated fatty acids. Examples of suitable saturated fatty acids include, but are not limited to, palmitic acid, stearic acid, arachidic acid, behenic acid, and lignoceric acid.

Suitable unsaturated fatty acids include olefinically unsaturated fatty acids having one or more double bonds in the fatty acid hydrocarbon backbone. In some embodiments, the unsaturated fatty acids have one to six double bonds. In other embodiments, the unsaturated fatty acids have one to four double bonds, one to three double bonds, or one to two double bonds. Each double bond can have either the cis or trans configuration. In some embodiments, the cis configuration is preferred.

Examples of unsaturated fatty acids suitable for use in the present invention are described in U.S. Pat. No. 5,219,733 and include, but are not limited to, 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid, α-eleostearic acid, β-eleostearic acid, punicic acid, 6,9,12 15-octadecatetraenoic acid, parinaric acid, 5,8,11,14-eicosatetraenoic acid, 5,8,11,14,17-eicosapentaenoic acid (EPA), 7,10,13,16,19-docosapentaenoic acid, 4,7,10,13,16,19-docosahexaenoic acid (DHA) and the like, and mixtures and derivatives thereof. Thus, in some embodiments of the invention, the fatty acid or fatty acid material comprises one or more unsaturated fatty acids selected from the group consisting of palmitoleic acid, oleic acid, linoleic acid, linolenic acid, eleostearic acid, ricinoleic acid, arachidonic acid, eicosapentaenoic acid, docosahexaenoic acid, cetoleic acid and erucic acid and mixtures and derivatives thereof. In a preferred embodiment, the fatty acid or fatty acid material comprises one or more unsaturated fatty acids selected from the group consisting of palmitoleic acid, oleic acid, linoleic acid, and linolenic acid, and mixtures and derivatives thereof.

Fatty acids suitable for use in the present invention also include derivates of unsaturated or saturated fatty acids, e.g., including, but not limited to, hydroxy derivatives of fatty acids, or "hydroxy fatty acids." Examples of useful hydroxy fatty acids are described in U.S. Pat. No. 5,219,733 and include, but are not limited to, α-hydroxylauric acid, α-hydroxymyristic acid, α-hydroxypalmitic acid, α-hydroxystearic acid, ω-hydroxylauric acid, α-hydroxyarachidic acid, 9-hydroxy-12-octadecenoic acid, ricinoleic acid, α-hydroxybehenic acid, 9-hydroxy-trans-10,12-octadecadienic acid, kamolenic acid, ipurolic acid, 9,10-dihydroxystearic acid, 12-hydroxystearic acid and the like.

The fatty acids useful in the present invention also can be optionally substituted with one or more moieties selected from the group consisting of hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, amino($C_{6-10}$)aryl($C_{1-26}$)alkyl, heteroaryl($C_{1-26}$)alkyl, $C_{3-6}$ cycloalkyl, phenyl($C_{1-26}$)alkyl, and a dioxanone ring and an oxirane (epoxy, or epoxide) ring formed between two adjacent chain carbons.

Thus, in some aspects of the present invention, the fatty acid or fatty acid material comprises saturated or unsaturated ($C_6$-$C_{32}$)alkyl carboxylic acids that are optionally substituted with one or more moieties selected from the group consisting of hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, amino($C_{6-10}$)aryl($C_{1-26}$)alkyl, heteroaryl($C_{1-26}$)alkyl, $C_{3-6}$ cycloalkyl, phenyl($C_{1-26}$)alkyl, and a dioxanone ring and an oxirane (epoxy, or epoxide) ring formed between two adjacent chain carbons.

In some embodiments, preferred fatty acids are optionally substituted with one or more moieties selected from the group consisting of a dioxanone or oxirane ring formed between two adjacent chain carbons. In other embodiments of the invention, preferred fatty acids are optionally substituted with one or more moieties selected from the group consisting of $C_{1-26}$ alkoxy, hydroxy, and hydroxy($C_{1-26}$)alkyl, or selected from the group consisting of amino($C_{1-26}$)alkyl, amino($C_{6-10}$)aryl, and amino($C_{6-10}$)aryl($C_{1-26}$)alkyl. In yet other embodiments, preferred fatty acids are optionally substituted with one or more moieties selected from the group consisting of hydrogen, $C_{1-26}$ alkyl, and $C_{3-26}$ alkenyl, or selected from the group consisting of $C_{6-10}$ aryl, heteroaryl, heteroaryl($C_{1-26}$)alkyl, $C_{3-6}$ cycloalkyl, and phenyl($C_{1-26}$)alkyl.

The fatty acids and fatty acid materials useful in the present invention can also be described by their physical characteristics. Useful parameters include solubility, iodine value, and, in particular, hydrophilic/lipophilic balance, since the fatty acids and fatty acid materials of the present invention are, in general, lipophilic and relatively non-water-soluble. For example, fatty acid materials preferred for use in the present invention have a hydrophilic/lipophilic balance of less than about 3.5. Values for hydrophilic/lipophilic balance can be calculated using the "Molecular Modeling Pro Plus" software (version 6.0.6, Norgwyn Montgomery Software Inc.) available from Chem SW, Fairfield, Calif.

Preferred fatty acid materials also have iodine values greater than about 50. Iodine values are well-known measures of the number of double bonds present in fatty ($C_6$-$C_{32}$)alkyl carboxylic acids and can be determined according to Method Tg1a-67, or calculated according to Method Cd1c-85, both as recited in the "Official Methods and Recommended Practices of the American Oil Chemists" Society, Fifth Edition, Second Printing, AOCS Press, Champaign, Ill., USA, which is incorporated by reference herein in its entirety. For example, the iodine value of oleic acid is 89; the iodine value of linoleic acid is 173, and the iodine value of linolenic acid is 262. Due to their high degrees of unsaturation, the iodine values of arachidonic acid, eicosapentaenoic acid and docosahexaenoic acid are all greater than the iodine value of linoleic acid.

The fatty acids and fatty acid materials useful in the present invention can also be described by Hansen solubility parameters. Hansen solubility parameters are described in detail in "Hansen Solubility Parameters: A User's Handbook," by Charles M. Hansen (CRC Press, 1999), which is incorporated by reference herein in its entirety. Preferred alkyl carboxylic acid materials for use in the present invention have Hansen polarity values of less than about 4 (delta/sqr(MPa)), or less than about 3.5 (delta/sqr(MPa)), and Hansen hydrogen bonding values of less than about 8 (delta/sqr(MPa)), or less than about 7.6 (delta/sqr(MPa)).

For example, preferred alkyl carboxylic acid materials can include, but are not limited to, those having Hansen polarity values between about 4.0 and about 1.0 (delta/sqr(MPa), or between about 4.0 and about 2.0 (delta/sqr(MPa)), or between about 3.5 and about 2.5 (delta/sqr(MPa)), and Hansen hydrogen bonding values between about 8.0 and about 5.0 (delta/sqr(MPa)), or between about 8.0 and about 6.0 (delta/sqr (MPa)). Especially preferred are those alkyl carboxylic acids or alkyl carboxylic acid materials having Hansen polarity values of less than about 3.5 (delta/sqr(MPa)) and Hansen hydrogen bonding values of less than about 7.6 (delta/sqr (MPa)). Hansen solubility parameters can be calculated using the program "Molecular Modeling Pro Plus" (version 6.0.6, Norgwyn Montgomery Software Inc., available from ChemSW, Inc.) based on values published in the Handbook of Solubility Parameters and Other Parameters by Allan F. M. Barton (CRC Press, 1983) for solvents obtained experimentally by Hansen.

The Hansen polarity values at 25° C. and Hansen hydrogen bonding values at 25° C. of several alkyl carboxylic acid materials suitable for use in the present invention are listed in Table 1.

Handbook of Solubility Parameters and Other Parameters by Allan F. M. Barton (CRC Press, 1983) for solvents obtained experimentally by Hansen.

The methods of the present invention utilize a carboxylic acid reductase enzyme to reduce fatty acids to their corresponding aldehydes. Examples of carboxylic acid reductase enzymes are those from *Nocardia* species, or those from certain *Neurospora* species (e.g., *Neurospora crassa* (Gross, G. & Zenk, M, *Eur. J. Biochem.* 8:420-425 (1969)) or from certain *Clostridium* species (e.g., *Clostridium thermoaceticum* (White, H., et al., *Eur. J. Biochem* 184:89-96 (1989))). In some aspects of the invention, the carboxylic acid reductase is a prokaryotic carboxylic acid reductase from a *Nocardia* species, e.g., *Nocardia asteroides*. The purification and characterization of carboxylic acid reductase from *Nocardia asteroides* is described in Kato, N. et al., *J. Agric. Biol. Chem.* 55:757-762 (1991). A preferred carboxylic acid reductase is the carboxylic acid reductase, or aryl aldehyde oxidoreductase, from *Nocardia* species strain NRRL 5646. This carboxylic acid reductase is described by Rosazza et al. in U.S. Pat. No. 6,261,814 B1 and in U.S. Pat. Appl. Publ. No. US 2004/0180400 A1. U.S. Pat. No. 6,261,814 B1 and U.S. Pat. Appl. Publ. No. US 2004/0180400 A1 are incorporated by reference herein in their entireties.

In some aspects of the present invention, the carboxylic acid reductase is present in its natural form. In some embodiments, the carboxylic acid reductase is isolated and purified prior to its use in the methods of the present invention. For example, methods for purifying the *Nocardia* sp. NRRL 5646 carboxylic acid reductase are described in Rosazza et al., U.S. Pat. No. 6,261,814 B1.

In other aspects, the carboxylic acid reductase is a recombinant carboxylic acid reductase. Examples of recombinant *Nocardia* sp. NRRL 5646 carboxylic acid reductase that are suitable for use in the present invention are described in Rosazza et al., U.S. Pat. Appl. Publ. No. US 2004/0180400 A1. U.S. Pat. Appl. Publ. No. US 2004/0180400 A1 also provides methods of making the recombinant enzyme. In some embodiments, the recombinant carboxylic acid reductase is isolated and purified prior to its use in the methods of the present invention.

In some aspects, the methods disclosed herein for preparing an aldehyde from its corresponding fatty acid further comprise incubating the fatty acid or fatty material and the carboxylic acid reductase. In some embodiments of the invention, the fatty acid or fatty acid material is incubated with the

TABLE 1

Hansen polarity values and Hansen hydrogen bonding values of several alkyl carboxylic acid materials.

| Hansen Solubility Parameters (25° C.) | oleic acid | linoleic acid | linolenic acid | arachidonic acid | eicosa- pentaenoic acid | docosa- hexaenoic acid |
|---|---|---|---|---|---|---|
| Polarity | 3.2384 | 3.31338 | 3.37669 | 3.13706 | 3.19388 | 2.97912 |
| Hydrogen bonding | 6.02164 | 6.51409 | 6.97265 | 7.07841 | 7.48207 | 7.53673 |

The Hansen 3-D solubility parameters in Table 1 were calculated using the program "Molecular Modeling Pro Plus" (version 6.0.6, Norgwyn Montgomery Software Inc., available from ChemSW, Inc.) based on values published in the carboxylic acid reductase for a period of time sufficient to reduce at least about 10%, about 20%, about 30%, about 40%, or about 50% of the fatty acid material to its corresponding aldehyde. In other embodiments, the fatty acid or fatty acid material is incubated with the carboxylic acid reductase for a period of time sufficient to reduce at least about 60%, about 70%, about 80%, about 90%, or about 95% of the fatty acid material to its corresponding aldehyde. In preferred embodiments, the fatty acid or fatty acid material is incubated with the carboxylic acid reductase for a period of time sufficient to reduce at least about 50% of the fatty acid material to its corresponding aldehyde.

Incubation can be performed under in vitro or in vivo conditions. For example, isolated carboxylic acid reductase can be used to convert fatty acids to their corresponding aldehydes according to the methods of the present invention by incubating the isolated enzyme with fatty acids under in vitro conditions. Examples of suitable reaction conditions for in vitro reactions are described in U.S. Pat. No. 6,261,814 B1 for reduction reactions of aryl carboxylic acids using isolated *Nocardia* sp. NRRL 5646 carboxylic acid reductase in aqueous systems, as well as in Example 1 below. Incubation can be carried out at temperatures ranging from about −25° C. to about 70° C. for times ranging from about 30 minutes to several days with our without agitation. For in vitro reactions using aqueous buffered solutions, suitable buffers include phosphate buffer, Tris buffer, BIS TRIS buffer, ADA buffer, ACES buffer. PIPES buffer, MOPSO buffer, BES buffer, MOPS buffer, HEPES buffer, TES buffer, DIPSO buffer, and TRISMA buffer. In addition, a non-aqueous solvent may be contacted with the aqueous buffered solution. Examples of such non-aqueous solvents include, but are not limited to, pentane, hexane, heptane, octane, petroleum ether, and isomers and mixtures thereof.

In other aspects of the present invention, incubation of the carboxylic acid reductase and the fatty acid or fatty acid material is performed under in vivo conditions. Example 1 below describes conditions suitable for in vivo reactions using *Nocardia* sp. NRRL 5646 in whole cells to convert oleic acid into its corresponding aldehyde forms. Use of whole cells to carry out enzymatic reactions is known to those of skill in the art. For example, the use of bacterial cells to carry out enzymatic reactions is described in European Patent application EP0187525 A2, "Process for producing L-serine" (Ajinomoto Co., Inc, Tokyo, Japan), which describes the enzymatic conversion of 2-oxo-oxazolidine-4-carboxylic acid (OOC) to L-lysine by incubation of whole *Bacillus licheniformis* cells with OOC.

In some aspects, the methods disclosed herein for preparing an aldehyde from its corresponding fatty acid further comprise separating the aldehyde from the fatty acid or fatty acid material.

The aldehyde can be separated from the fatty acid or fatty acid material using methods known to those of skill in the art. Examples of suitable purification methods include, but are not limited to, distillation and chromatography, including simulated moving bed chromatography.

The aldehydes produced using the methods of the present invention have structures that correspond to the structures of the fatty acid. As described above, the aldehydes produced have hydrocarbon backbones from about 4 to 32 carbon atoms long and be saturated, or unsaturated, or optionally substituted with one or more moieties selected from the group consisting of hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, amino($C_{6-10}$)aryl($C_{1-26}$)alkyl, heteroaryl($C_{1-26}$)alkyl, $C_{3-6}$ cycloalkyl, phenyl($C_{1-26}$)alkyl, and a dioxanone ring and an oxirane (epoxy or epoxide) ring formed between two adjacent chain carbons.

Thus, in some aspects of the present invention, the aldehydes produced using the methods of the present invention include, but are not limited to ($C_6$-$C_{32}$)aldehydes of Formula I:

wherein, in each instance, A, B and C are independently selected from the group consisting of:

(i)
$$—(CR_2)—,$$

(ii)

wherein, one of $R^2$ and $R^3$ is a carbonyl and the other of $R^2$ and $R^3$ is $CR^4R^5$, and wherein $R^4$ and $R^5$ are independently selected from the group consisting of hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, amino($C_{6-10}$)aryl($C_{1-26}$)alkyl, heteroaryl($C_{1-26}$)alkyl, $C_{3-6}$ cycloalkyl and phenyl($C_{1-26}$)alkyl;

(iii)
$$(—\underset{R}{\underset{|}{C}}=\underset{R}{\underset{|}{C}}—),$$

(iv)
$$(—\triangle—), \text{ and}$$

(v)
$$(—\underset{R}{\underset{|}{C}}=\underset{R}{\underset{|}{C}}—\underset{R}{\underset{|}{C}}=\underset{R}{\underset{|}{C}}—);$$

wherein, R is, in each instance, independently selected from the group consisting of: hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, amino($C_{6-10}$)aryl($C_{1-26}$)alkyl, heteroaryl($C_{1-26}$)alkyl,$C_{3-6}$ cycloalkyl and phenyl($C_{1-26}$)alkyl;

x is an integer from 5 to 10; and n is an integer from 1 to 6.

In some embodiments, preferred ($C_6$-$C_{32}$)aldehydes of Formula I are those wherein one of $R^2$ and $R^3$ of (ii) is a carbonyl and the other of R and $R^3$ is $CR^4R^5$, and wherein $R^4$ and $R^5$ are independently selected from the group consisting of hydrogen, $C_{1-26}$ alkyl, $C_{3-26}$ alkenyl, and $C_{1-26}$ alkoxy.

Thus, in some aspects of the present invention, the aldehydes produced using the methods of the present invention include, but are not limited to ($C_6$-$C_{32}$)aldehydes of Formula I:

(I)

wherein, in each instance, A, B and C are independently selected from the group consisting of:

(i)

(ii)

wherein, one of $R^2$ and $R^3$ is a carbonyl and the other of $R^2$ and $R^3$ is $CR^4R^5$, and wherein $R^4$ and $R^5$ are independently selected from the group consisting of hydrogen, $C_{1-26}$ alkyl, $C_{3-26}$ alkenyl, and $C_{1-26}$ alkoxy;

(iii)

(iv)

and

(v)

wherein, R is, in each instance, independently selected from the group consisting of hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, amino($C_{6-10}$)aryl($C_{1-26}$)alkyl, heteroaryl($C_{1-26}$)alkyl, $C_{3-6}$ cycloalkyl and phenyl($C_{1-26}$)alkyl;

x is an integer from 5 to 10; and n is an integer from 1 to 6.

In other embodiments, preferred ($C_6$-$C_{32}$)aldehydes of Formula I are those in which A, B, and C are independently (i)

(iii)

or

(v)

Especially preferred are those aldehydes in which A, B, and C are independently (iii)

, or (v)

Aldehydes in which A, B, and C of Formula I are independently (iii) or (v) include all stereoisomers of the aldehydes, e.g., includes those aldehydes having either cis or trans stereochemistry about each double bond. Particularly preferred are those aldehydes having cis stereochemistry.

In yet other embodiments, preferred ($C_6$-$C_{32}$)aldehydes of Formula I are those in which A, B, and C are independently (ii)

wherein, one of $R^2$ and $R^3$ is a carbonyl and the other of $R^2$ and $R^3$ is $CR^4R^5$, and wherein $R^4$ and $R^5$ are independently selected from the group consisting of hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, amino($C_{6-10}$)aryl($C_{1-26}$)alkyl, heteroaryl($C_{1-26}$)alkyl, $C_{3-6}$ cycloalkyl and phenyl($C_{1-26}$)alkyl; or (iv)

In these embodiments, preferred ($C_6$-$C_{32}$)aldehydes of Formula I are those wherein one of $R^2$ and $R^3$ of (ii) is a carbonyl and the other of $R^2$ and $R^3$ is $CR^4R^5$, and wherein $R^4$ and $R^5$ are independently selected from the group consisting of hydrogen, $C_{1-26}$ alkyl, $C_{3-26}$ alkenyl, and $C_{1-26}$ alkoxy.

In some embodiments, preferred values of R are selected from the group consisting of $C_{1-26}$ alkoxy, hydroxy, and hydroxy($C_{1-26}$)alkyl, or selected from the group consisting of amino ($C_{1-26}$)alkyl, amino($C_{6-10}$)aryl, and amino($C_{6-10}$)aryl ($C_{1-26}$)alkyl. In yet other embodiments, preferred values of R are selected from the group consisting of hydrogen, $C_{1-26}$ alkyl, and $C_{3-26}$ alkenyl, or selected from the group consisting of $C_{6-10}$ aryl, heteroaryl, heteroaryl($C_{1-26}$)alkyl, $C_{3-6}$ cycloalkyl, and phenyl($C_{1-26}$)alkyl.

Preferred values of $R^4$ and $R^5$ are independently selected from the group consisting of hydrogen, $C_{1-26}$ alkyl, $C_{3-26}$ alkenyl, and $C_{1-26}$ alkoxy.

Preferred values of x are 5 to 9, 6 to 9, or 7 to 9. Preferred values of n are 1 to 5, 1 to 4, or 1 to 3.

The following example is illustrative, but not limiting, of the methods and compositions of the present invention. Other suitable modifications and adaptations of the variety of conditions and parameters normally encountered and obvious to those skilled in the art are within the spirit and scope of the invention.

EXAMPLES

Example 1

Recombinant carboxylic acid reductase (CAR) from *Nocardia* sp. NRRL 5646 was tested for its ability to reduce oleic acid under in vivo and in vitro conditions.

Materials and Methods

Chromatography: Organic solvents were obtained from Fisher scientific. Thin Layer Chromatography (TLC) was carried on Silica gel on polyester plates (0.25 mm Aldrich) or on Glass Plates (0.25 mm, Whatman). TLC plates were developed in solvent mixture of hexanes: ethylacetate: glacial acetic acid (75:25:0.1 v/v/v) and visualized by spraying with either p-anisaldehyde stain (0.5 mL of p-anisaldehyde and 0.5 mL of $H_2SO$ in 60 mL methanol) or with phosphomolybdic acid (7% (w/v)) in ethanol followed by heating.

Fermentation and screening procedures: *E. coli* BL21 Codon Plus® (DE3) RP/pPV 1.184 (car+sfp) cultures were prepared as described in US Pat. Appl. Publ. No. 2004/0180400 A1, which is incorporated by reference herein in its entirety.

All solutions were prepared in distilled, deionized water. LB medium (1 L) contained Bacto tryptone (10 g), Bacto yeast extract (5 g), and NaCl (10 g). Ampicillin (Ap) stock solutions (100 mg/mL) were sterilized through 0.22-µm membranes (Millipore). Chloramphenicol (Cm) (34 mg/mL) was prepared by dissolving in 95% ethanol.

For in vivo reductions, *E. coli* BL21 Codon Plus® (DE3) RP/pPV 1.184 (car+sfp) cultures were initiated by inoculating a tiny crystal from the glycerol freeze into 10 mL LB medium containing Ap (100 µg/mL) and Cm (34 µg/mL) in a stainless steel-capped 25 mL Delong flask. The cultures were incubated with shaking at 250 rpm on New Brunswick Scientific G25 Gyrotory shaker for 16 h at 37° C. 10% inoculum derived from this overnight grown culture was inoculated in 200 mL LB medium containing Ap (100 µg/mL) and Cm (34 µg/mL). The cultures were incubated in 37° C., 250 rpm for 4 hours before receiving oleic acid (200 mg) as substrate. A control was prepared consisting of sterile medium incubated with the organism but without substrate.

5 mL samples were withdrawn from the cultures at various time intervals, acidified to pH 2, extracted with ethyl acetate (2×5 mL), and the organic layer separated. The organic layer was then removed, evaporated to dryness and reconstituted in 0.5 mL ethyl acetate. Samples were spotted onto TLC plates for analysis.

For in vitro reductions, reactions were carried out in 50 mM Tris buffer (pH 7.5), 1 mM EDTA, 10 mM $MgCl_2$, 1 mM DTT, 10% (v/v) glycerol, 5 mM ATP, 0.4 mM NADPH, and 5 mM oleic acid in a final volume of 50 mL. The oleic acid substrate was dissolved in 50 µL of DMF and added to the stirred solution. The pH of the solution was adjusted to 7.5 before addition of substrate. The solution was stirred at 100 rpm at room temperature (rt) for 10 min before the enzyme was added. 1 mg of purified recombinant CAR (specific activity (sp. act.) 0.26 units/mg) was added to this solution and incubated for 6 h. Purification of CAR was carried out as described in U.S. Pat. Appl. Publ. No. 2004/0180400 A1, which is incorporated by reference herein in its entirety.

2 mL samples were withdrawn, acidified to pH 2, extracted with ethyl acetate (2×5 mL), and the organic layer separated. The organic layer was then removed, evaporated to dryness and reconstituted in 0.5 mL ethyl acetate. Samples were spotted onto TLC plates for analysis.

Results

Figure 1A:
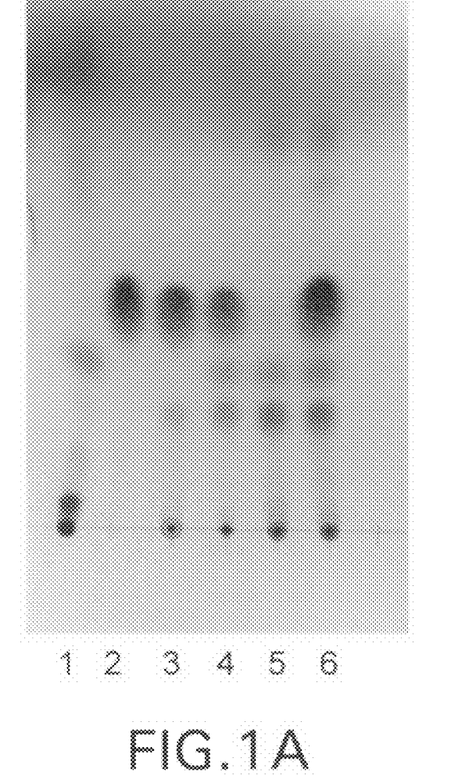
FIG. 1A presents the results of TLC analysis of bacterial culture aliquots sampled at 4 hours (Lane 3), 8 hours (Lane 4), or 24 hours (Lane 5) after the addition of oleic acid.
Figure 1B:
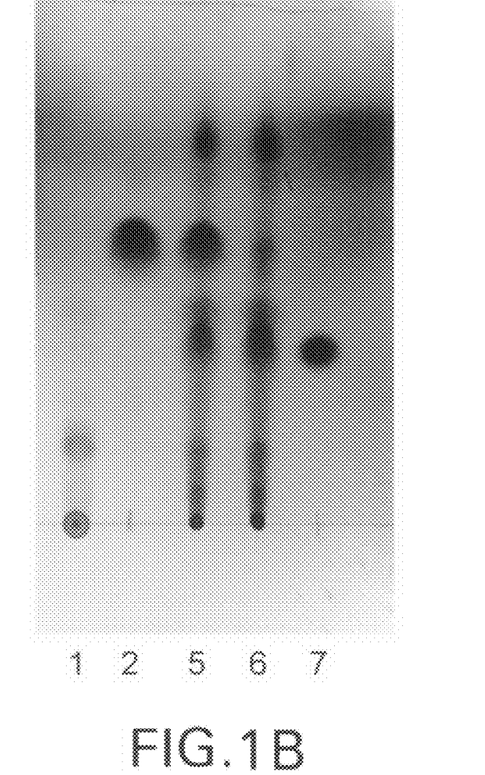
FIG. 1B presents the results for a 24 hour sample (Lane 5 and Lane 6) with oleic acid (Lane 2) and octadecanol (Lane 7) standards. TLC plates were visualized by staining with phosphomolybdic acid.
Figure 1C:
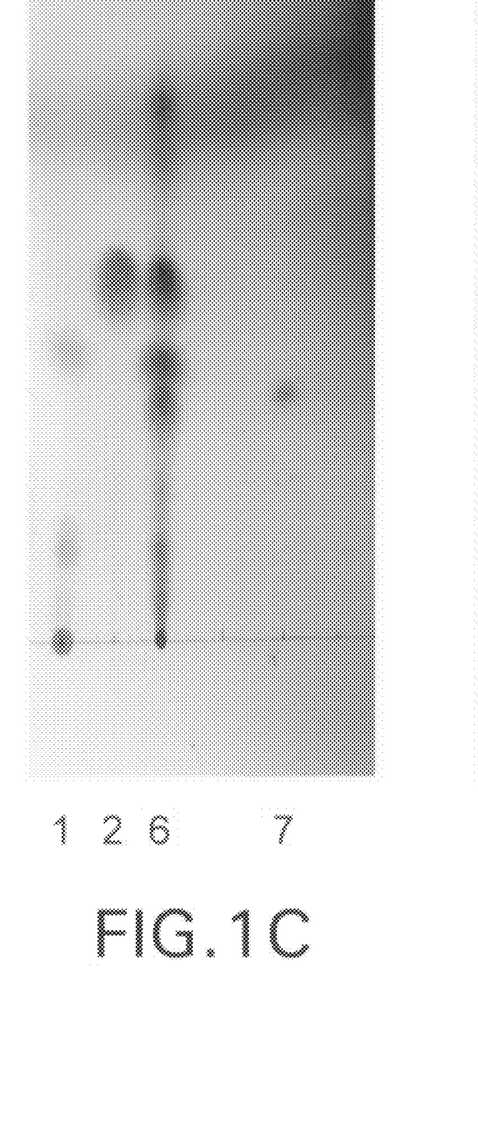
FIG. 1C presents the results for a 24 hour sample (Lane 6) with oleic acid (Lane 2) and octadecanol (Lane 7) controls. TLC plates were visualized by staining with phosphomolybdic acid.
Figure 1D:
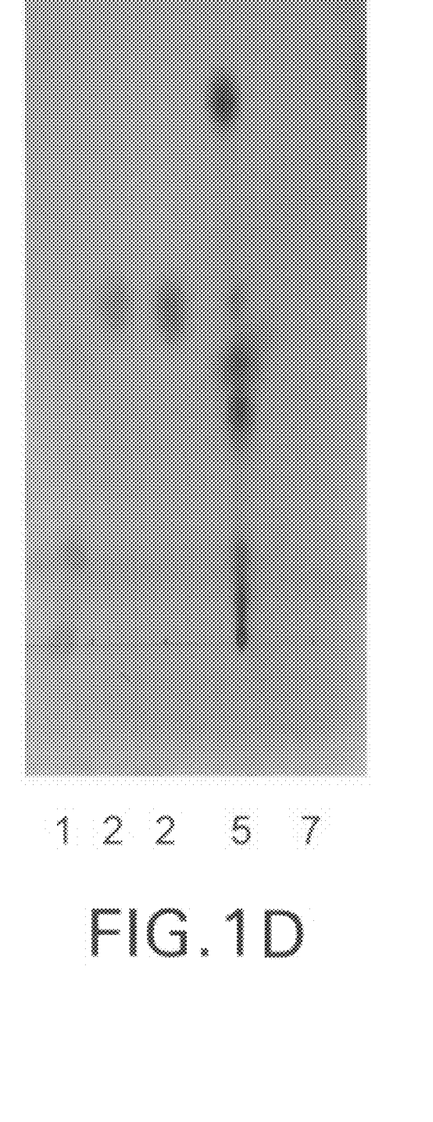
FIG. 1D presents the TLC results for a 24 hour sample (Lane 5), with oleic acid (Lane 2) and octadecanol (Lane 7) standards. The TLC plate was visualized by staining with p-anisaldehyde.
Figure 2A:
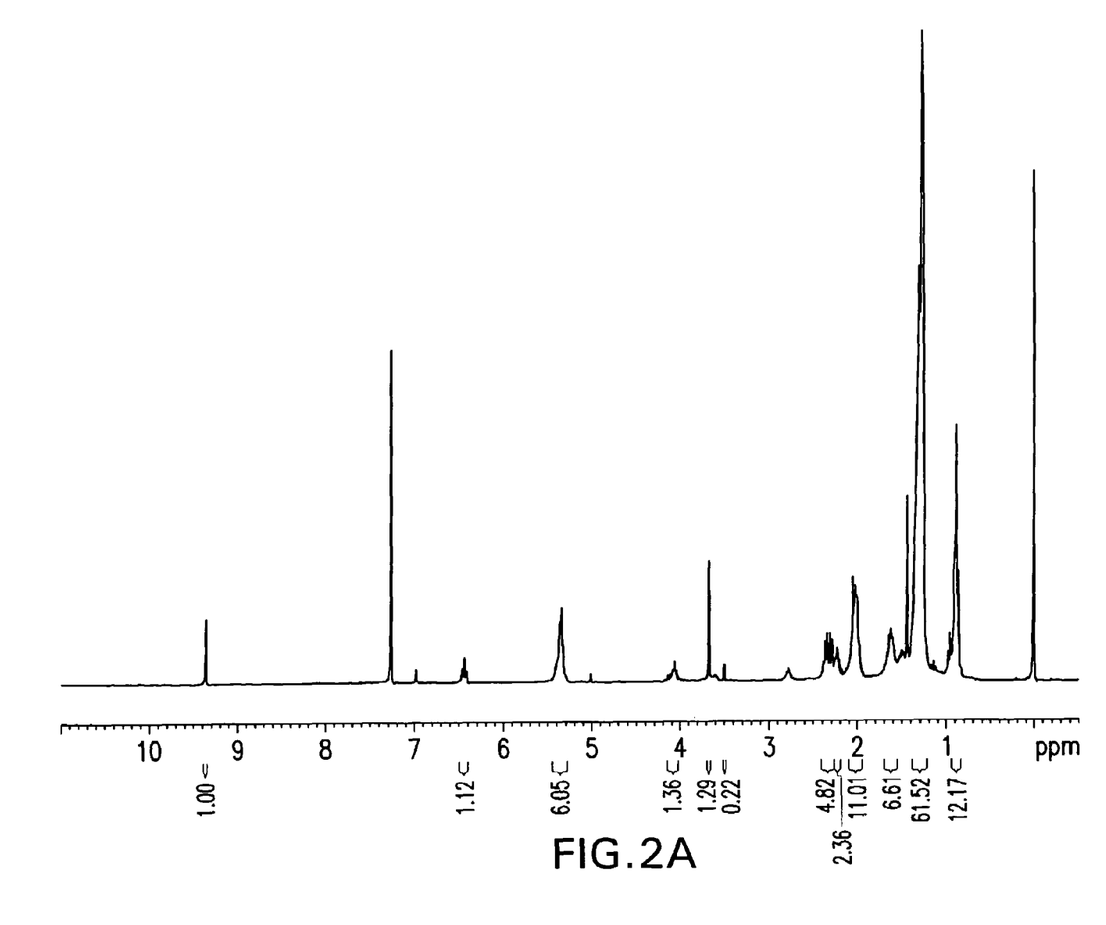
Figure 2B:
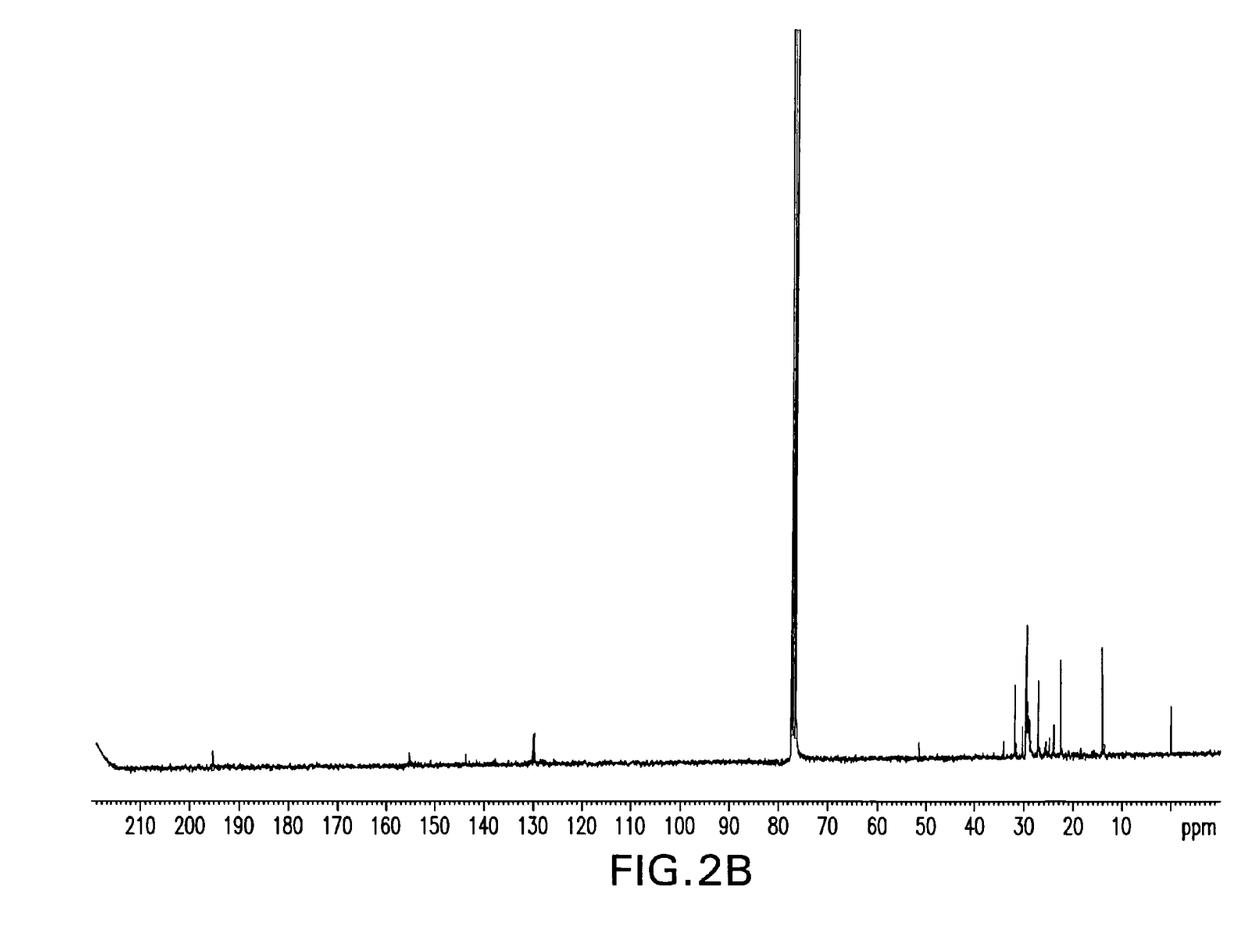
FIG. 2B presents the $^{13}$C spectrum for Fraction 1.

In vivo reduction of oleic acid: TLC analysis of samples taken from various aliquots indicated that oleic acid was consumed over a 24 h period. Two new spots were also observed concurrently at $R_f$=0.74 and 0.38. ($R_f$ for oleic acid=0.56; $R_f$ for octadecanol=0.34.) After 24 h of growth, the culture was acidified with 6N HCl to pH 2 and extracted with ethyl acetate (3×200 mL). The combined organic extract was washed with brine, dried over $Na_2SO_4$ and concentrated in vacuo. The extract (50 mg) was further purified by thin layer chromatography to yield 3 mg of Fraction 1 ($R_f$=0.74), 10 mg of Fraction 2 ($R_f$=0.56) and 3 mg of Fraction 3 ($R_f$=0.38) (FIG. 1). $^1H$ NMR and $^{13}C$ NMR analysis of the fraction of $R_f$=0.74 (Fraction 1) showed a peak corresponding to an aldehyde moiety (FIG. 2).

Figure 3:
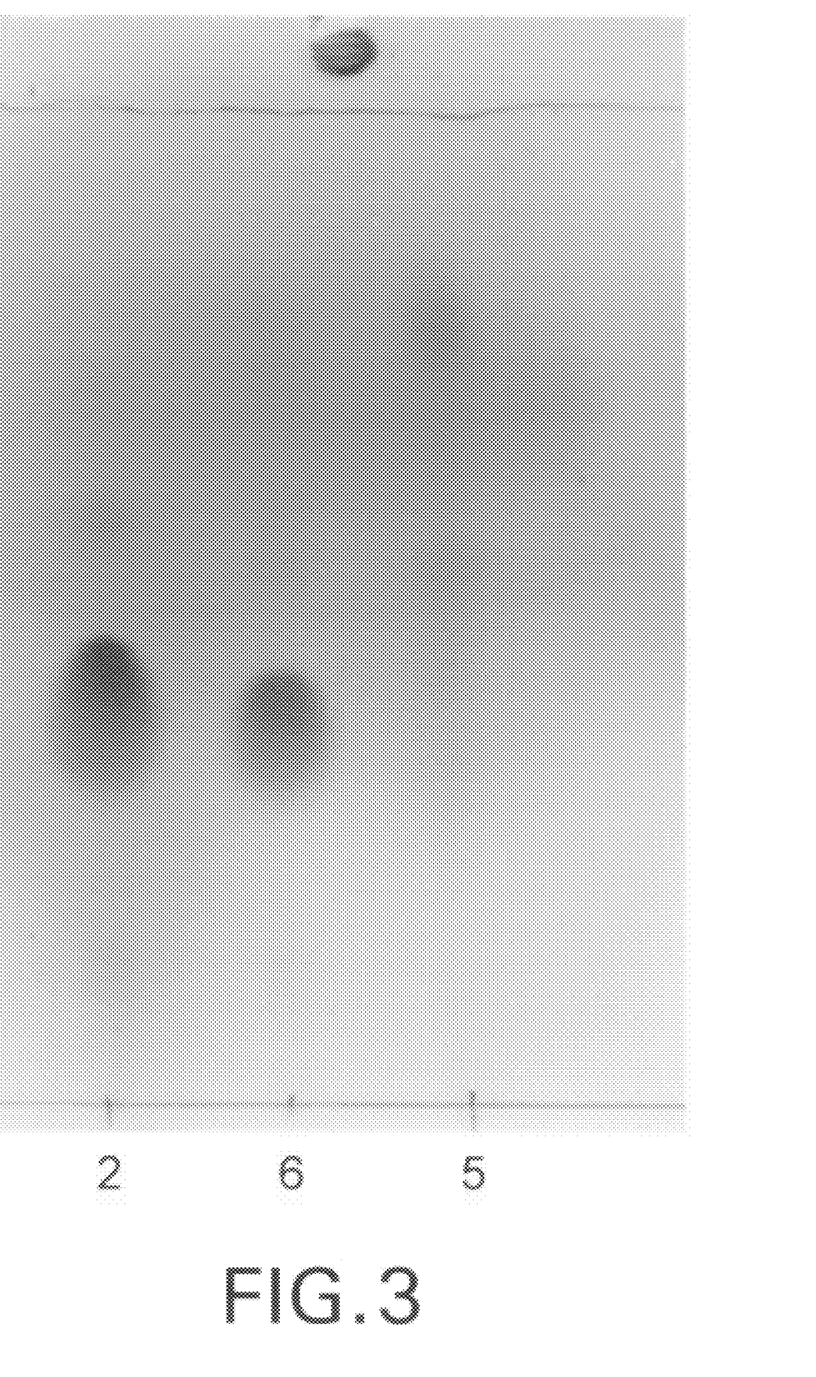
FIG. 3 presents the results of TLC analysis of the reaction mixture taken during the course of the in vitro reduction experiment described in Example 1. An aliquot of the reaction mixture was taken 1 hour after incubation of oleic acid with purified recombinant CAR and analyzed by TLC. Key: Lane 2: oleic acid standard; Lane 6: reaction mixture+oleic acid standard; Lane 5: reaction mixture.

In vitro reduction of oleic acid: In vitro reduction of oleic acid by purified CAR gave a spot of $R_f$=0.78 on TLC, but the reaction did not go to completion and the majority of the starting material was recovered (FIG. 3). The poor reaction may have been due to the poor solubility of the starting material in the reaction mixture.

All documents, e.g., scientific publications, patents, patent applications and patent publications, recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

What is claimed is:

1. A method of preparing a ($C_6$-$C_{32}$)aldehyde from a fatty ($C_6$-$C_{32}$)alkyl carboxylic acid material derived from a vegetable oil or an animal oil, the method comprising contacting the fatty ($C_6$-$C_{32}$)alkyl carboxylic acid material with a carboxylic acid reductase;
wherein the ($C_6$-$C_{32}$)aldehyde is prepared.

2. The method of claim 1, wherein the vegetable oil or animal oil is selected from the group consisting of butterfat, cocoa butter, cocoa butter substitutes, illipe fat, kokum butter, milk fat, mowrah fat, phulwara butter, sal fat, shea fat, borneo tallow, lard, lanolin, beef tallow, mutton tallow, tallow, animal fat, canola oil, castor oil, coconut oil, coriander oil, corn oil, cottonseed oil, hazelnut oil, hempseed oil, jatropha oil, linseed oil, mango kernel oil, meadowfoam oil, mustard oil, neat's foot oil, olive oil, palm oil, palm kernel oil, peanut oil, rapeseed oil, rice bran oil, safflower oil, sasanqua oil, shea butter, soybean oil, sunflower seed oil, tall oil, tsubaki oil, tung oil, vegetable oils, marine oils, menhaden oil, candlefish oil, cod-liver oil, orange roughy oil, pile herd oil, sardine oil, whale oils, herring oils, triglyceride, diglyceride, monoglyceride, triolein palm olein, palm stearin, palm kernel olein, palm kernel stearin, triglycerides of medium chain fatty acids, and derivatives, conjugated derivatives, genetically-modified derivatives and mixtures thereof.

3. The method of claim 1, wherein the fatty ($C_6$-$C_{32}$)alkyl carboxylic acid material comprises a fatty ($C_6$-$C_{32}$)alkyl carboxylic acid.

4. The method of claim 1, wherein the fatty ($C_6$-$C_{32}$)alkyl carboxylic acid material comprises one or more fatty ($C_6$-$C_{32}$)alkyl carboxylic acids independently selected from the group consisting of palmitoleic acid, oleic acid, linoleic acid, linolenic acid, eleostearic acid, ricinoleic acid, arachidonic acid, cetoleic acid, eicosapentaenoic acid, docosahexaenoic acid, and erucic acid, and derivatives and mixtures thereof.

5. The method of claim 1, wherein the fatty ($C_6$-$C_{32}$)alkyl carboxylic acid material comprises one or more fatty ($C_6$-$C_{32}$)alkyl carboxylic acids independently selected from the group consisting of 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid, α-eleostearic acid, β-eleostearic acid, punicic acid, 6,9,12,15-octadecatetraenoic acid, parinaric acid, 5,8,11,14-eicosatetraenoic acid, 5,8,11,14,17-eicosapentaenoic acid (EPA), 7,10,13,16,19-docosapentaenoic acid, 4,7,10,13,16,19-docosahexaenoic acid (DHA), and derivatives and mixtures thereof.

6. The method of claim 1, wherein the fatty ($C_6$-$C_{32}$)alkyl carboxylic acid material comprises one or more fatty ($C_6$-$C_{32}$)alkyl carboxylic acids independently selected from the group consisting of α-hydroxylauric acid, α-hydroxymyristic acid, α-hydroxypalmitic acid, α-hydroxystearic acid, α-hydroxylauric acid, α-hydroxyarachic acid, 9-hydroxy-12-octadecenoic acid, ricinoleic acid, α-hydroxybehenic acid, 9-hydroxy-trans-10,12-octadecadienic acid, kamolenic acid, ipurolic acid, 9,10-dihydroxystearic acid, and 12-hydroxystearic acid.

7. The method of claim 1, wherein the fatty ($C_6$-$C_{32}$)alkyl carboxylic acid material has a hydrophilic/lipophilic balance of less than about 3.5.

8. The method of claim 1, wherein the fatty ($C_6$-$C_{32}$)alkyl carboxylic acid material has a Hansen polarity value of less than about 4 and a Hansen hydrogen bonding value of less than about 8.

9. The method of claim 1, wherein the fatty ($C_6$-$C_{32}$)alkyl carboxylic acid material has an iodine value greater than about 50.

10. The method of claim 1, wherein the reductase is isolated from the group consisting of a *Nocardia* species, a *Neurospora* species, and a *Clostridium* species.

11. The method of claim 10, wherein the reductase is isolated from a *Nocardia* species.

12. The method of claim 11, wherein the reductase is isolated from *Nocardia* sp. NRRL 5646.

13. The method of claim 1, wherein the reductase is a recombinant reductase.

14. The method of claim 1, further comprising incubating the fatty ($C_6$-$C_{32}$)alkyl carboxylic acid material and the carboxylic acid reductase for a period of time sufficient to reduce at least about 50% of the carboxylic acid material to the ($C_6$-$C_{32}$)aldehyde.

15. The method of claim 14, further comprising separating the ($C_6$-$C_{32}$)aldehyde from the fatty ($C_6$-$C_{32}$)alkyl carboxylic acid material.

16. The method of claim 1, wherein the ($C_6$-$C_{32}$)aldehyde has Formula I:

wherein, in each instance, A, B and C are independently selected from the group consisting of:

(i) $—(CR^2)—$, (ii) 
$$\underset{(}{\overset{R^2-R^3}{\underset{O\quad\quad O}{\diagdown\diagup}}}\underset{)}{},$$

wherein, one of $R^2$ and $R^3$ is a carbonyl and the other of $R^2$ and $R^3$ is $CR^4R^5$, and wherein $R^4$ and $R^5$ are independently selected from the group consisting of hydrogen, $C_{1-26}$ alkyl, $C_{3-26}$ alkenyl, and $C_{1-26}$ alkoxy, (iii) 
$$(—\underset{R}{\overset{R}{C}}=\underset{R}{\overset{R}{C}}—),$$

(iv) 
$$(\underset{}{\overset{O}{\triangle}}), \text{ and}$$

(v) 
$$(—\underset{R}{\overset{R}{C}}=\underset{R}{\overset{R}{C}}—\underset{R}{\overset{R}{C}}=\underset{R}{\overset{R}{C}}—);$$

wherein, R is, in each instance, independently selected from the group consisting of: hydrogen, $C_{1-26}$ alkyl, $C_{3-26}$ alkenyl, $C_{1-26}$ alkoxy, $C_{6-10}$ aryl, hydroxy, hydroxy($C_{1-26}$)alkyl, amino($C_{1-26}$)alkyl, amino($C_{6-10}$)aryl, heteroaryl, amino($C_{6-10}$)aryl($C_{1-26}$)alkyl, heteroaryl($C_{1-26}$)alkyl, $C_{3-6}$ cycloalkyl and phenyl($C_{1-26}$)alkyl;

x is an integer from 5 to 10; and n is an integer from 1 to 6.

17. The method of claim 16, wherein A, B, and C are independently selected from the group consisting of (i) $—(CR^2)—$, (iii) 
$$(—\underset{R}{\overset{R}{C}}=\underset{R}{\overset{R}{C}}—), \text{ and}$$

(v) 
$$(—\underset{R}{\overset{R}{C}}=\underset{R}{\overset{R}{C}}—\underset{R}{\overset{R}{C}}=\underset{R}{\overset{R}{C}}—).$$

18. A ($C_6$-$C_{32}$) aldehyde of Formula I:

wherein, in each instance, A, B and C are independently selected from the group consisting of:

(i) $—(CR^2)—$,

-continued (ii)

wherein, one of $R^2$ and $R^3$ is a carbonyl and the other of $R^2$ and $R^3$ is $CR^4R^5$, and wherein $R^4$ and $R^5$ are independently selected from the group consisting of hydrogen, $C_{1-26}$ alkyl, $C_{3-26}$ alkenyl, and $C_{1-26}$ alkoxy, (iii)

(iv)

(v)

wherein, R is, in each instance, independently selected from the group consisting of: hydrogen, $C_{1-26}$ alkyl, $C_{3-26}$ alkenyl, $C_{1-26}$ alkoxy, $C_{6-10}$ aryl, hydroxy, hydroxy$(C_{1-26})$alkyl, amino$(C_{1-26})$alkyl, amino$(C_{6-10})$aryl, heteroaryl, amino$(C_{6-10})$aryl$(C_{1-26})$alkyl, heteroaryl$(C_{1-26})$alkyl, $C_{3-6}$ cycloalkyl and phenyl$(C_{1-26})$alkyl;

x is an integer from 5 to 10; and n is an integer from 1 to 6.

19. The $(C_6-C_{32})$aldehyde of claim 18, wherein A, B, and C are independently selected from the group consisting of (i)

(iii)

(v)

* * * * *